United States Patent
Kimura et al.

(10) Patent No.: US 9,854,967 B2
(45) Date of Patent: Jan. 2, 2018

(54) GAZE DETECTOR

(71) Applicant: Panasonic Intellectual Property Management Co., Ltd., Osaka (JP)

(72) Inventors: Masayuki Kimura, Osaka (JP); Tadashi Shibata, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 256 days.

(21) Appl. No.: 14/940,847

(22) Filed: Nov. 13, 2015

(65) Prior Publication Data
US 2016/0066782 A1    Mar. 10, 2016

Related U.S. Application Data

(63) Continuation of application No. PCT/JP2015/001260, filed on Mar. 9, 2015.

(30) Foreign Application Priority Data

Mar. 13, 2014  (JP) .................. 2014-049642

(51) Int. Cl.
  *G06K 9/00*  (2006.01)
  *A61B 3/113*  (2006.01)
  (Continued)

(52) U.S. Cl.
  CPC ............ *A61B 3/113* (2013.01); *A61B 3/0025* (2013.01); *A61B 3/145* (2013.01); *A61B 5/0077* (2013.01);
  (Continued)

(58) Field of Classification Search
  CPC ............................ A61B 3/113; G06K 9/00597
  (Continued)

(56) References Cited

U.S. PATENT DOCUMENTS 5,859,921 A * 1/1999 Suzuki ............... G06K 9/00268
                                                                382/118
2009/0304232 A1    12/2009 Tsukizawa

FOREIGN PATENT DOCUMENTS

JP     2001-134371     5/2001
JP     2008-210239     9/2008
(Continued)

OTHER PUBLICATIONS

International Search Report of PCT application No. PCT/JP2015/001260 dated Mar. 31, 2015.

*Primary Examiner* — Hung Dang
(74) *Attorney, Agent, or Firm* — Wenderoth, Lind & Ponack, L.L.P.

(57) ABSTRACT

A detector detects head postures and gaze directions from images of a person to be measured captured by an imaging unit; a generation unit generates a gaze direction distribution with respect to each of the head postures, from the head postures and the gaze directions detected by the detector; a calibration unit determines predetermined one of the head postures as a reference posture, and calculates calibration parameters to be used to calibrate the gaze direction distribution with respect to the reference posture; and a correction unit corrects the gaze direction distributions with respect to the head postures other than the reference posture by using the calibration parameters calculated by the calibration unit. This reduces the influence on the calibration which may vary due to change in the head posture.

7 Claims, 7 Drawing Sheets

(51) Int. Cl.
 *G06F 3/01* (2006.01)
 *A61B 3/00* (2006.01)
 *A61B 3/14* (2006.01)
 *A61B 5/00* (2006.01)

(52) U.S. Cl.
 CPC .............. *G06F 3/012* (2013.01); *G06F 3/013* (2013.01); *G06K 9/00248* (2013.01); *G06K 9/00604* (2013.01); *A61B 2560/0223* (2013.01)

(58) Field of Classification Search
 USPC ........ 351/210, 209, 205, 246; 382/118, 117, 382/115
 See application file for complete search history.

(56) References Cited

FOREIGN PATENT DOCUMENTS

| | | |
|---|---|---|
| JP | 2008-237625 | 10/2008 |
| WO | 2008/007781 | 1/2008 |

\* cited by examiner

GAZE DETECTOR

BACKGROUND

1. Technical Field

The present disclosure relates to a gaze detector which detects a gaze direction of an object from a captured face image, in particular, relates to a technology which reduces effect caused by the difference between a head posture at a time of performing calibration and that in actual use after calibration.

2. Description of the Related Art

As a method for detecting a gaze direction, there is widely used a corneal reflection method in which infrared light is projected to an eye of a person to be measured and a gaze direction is detected from a positional relationship between a reflection image (called as a Purkinje image) of the infrared light formed on a cornea and a pupil center. However, detection of the gaze direction using an image is affected by personal difference in a shape or thickness of a cornea or the like or affected by outfits such as eyeglasses or contact lenses.

Depending on a shape or material of an outfit such as eyeglasses, the effects of refraction may vary at different angles. In such a case, every time a head posture changes, in other words, every time the outfit is equipped and removed, the state when calibration is performed varies; therefore, it is necessary to perform calibration every time the outfit is equipped and removed, and as a result, a person to be measured has to bear a heavy burden.

In a normal calibration process, a plurality of standard points need to be looked at when calibration is performed again; however, Unexamined Japanese Patent Publication No. 2001-134371 discloses a method in which only any one of the points needs to be looked at to estimate whole errors.

SUMMARY

A gaze detector according to the present disclosure is equipped with: an imaging unit configured to capture images of a person to be measured; a detector configured to detect head postures and gaze directions of the person to be measured from the images captured by the imaging unit; a generation unit configured to generate a gaze direction distribution with respect to each of the head postures from the head postures and the gaze directions detected by the detector; a calibration unit configured to select at least one reference posture from the head postures and configured to calculate calibration parameters by using the gaze direction distributions which correspond to the at least one reference posture; and a correction unit configured to correct the gaze direction distributions with respect to the head postures other than the reference posture, by using the calibration parameters calculated by the calibration unit.

A gaze detector is provided in which the effect due to change in the head posture can be automatically corrected with the above configuration.

DETAILED DESCRIPTION

Exemplary embodiments will be described in detail below with reference to the drawings as needed. However, an unnecessarily detailed description may be omitted. For example, a detailed description of an already well-known item and a repeated description of substantially identical components may be omitted. This is for avoiding the following description from becoming unnecessarily redundant and for making the description easier for a person skilled in the art to understand.

Note that the inventors provide the accompanying drawings and the following description to help those skilled in the art to sufficiently understand the present disclosure, and do not intend to use the drawings or description to limit the subject matters of the claims.

First Exemplary Embodiment

In the following, a first exemplary embodiment will be described with reference to FIGS. 1 to 9.

[1-1. Configuration]

Figure 1:
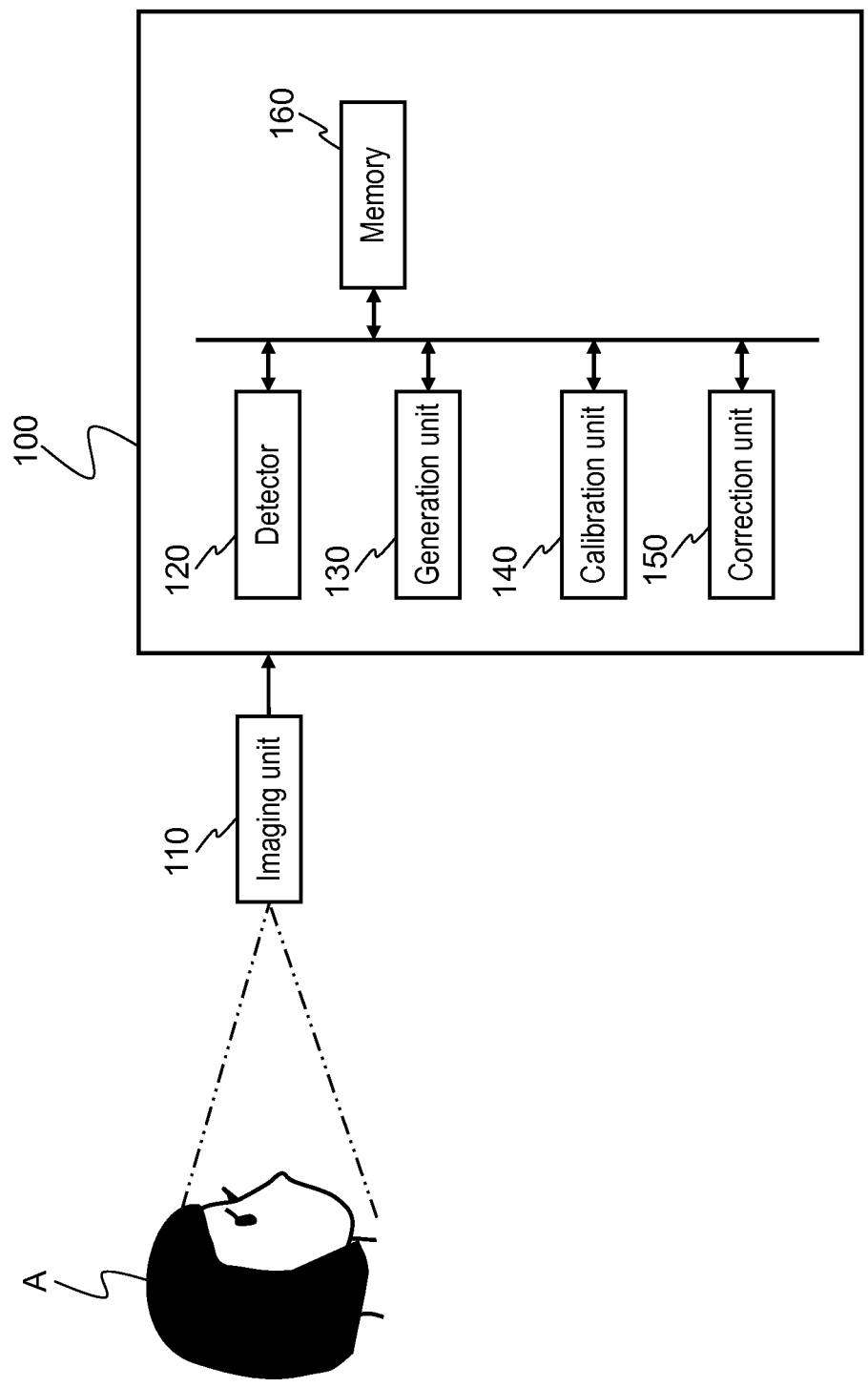
FIG. 1 is a block diagram showing a configuration of a gaze detector in a first exemplary embodiment of the present disclosure.

FIG. 1 is a block diagram showing a configuration of a gaze detector in the first exemplary embodiment.

Gaze detector 100 is equipped with imaging unit 110, detector 120, generation unit 130, calibration unit 140, correction unit 150, and memory 160.

Imaging unit 110 captures images of person A to be measured. Imaging unit 110 includes a video camera, a lighting device, and the like. A number of the video cameras may be one or more than one. Imaging unit 110 can be disposed anywhere as long as it is possible to capture images of a face of person A to be measured from a direction as close to a front direction as possible.

Detector 120 detects head postures and gaze directions of person A to be measured from the images captured by imaging unit 110. Detector 120 can be realized by hardware such as a DSP or a microcomputer, or by a combination of hardware and software, for example.

Generation unit 130 generates a gaze direction distribution with respect to each of the head postures, from the head postures and the gaze directions detected by detector 120.

Calibration unit 140 selects at least one head posture as a reference posture and calculates calibration parameters by using the gaze direction distribution with respect to the reference posture of the gaze direction distributions, each of which is generated by generation unit 130 with respect to each of the head postures. For example, the most frequent head posture is selected as the reference posture.

Correction unit 150 corrects the gaze direction distributions with respect to the head postures other than the reference posture by using the calibration parameters calculated by calibration unit 140.

Memory 160 is used as a working memory of detector 120 and includes a DRAM or the like.

[1-2. Operation]

An operation of gaze detector 100 configured as above will be described below.

Figure 2:
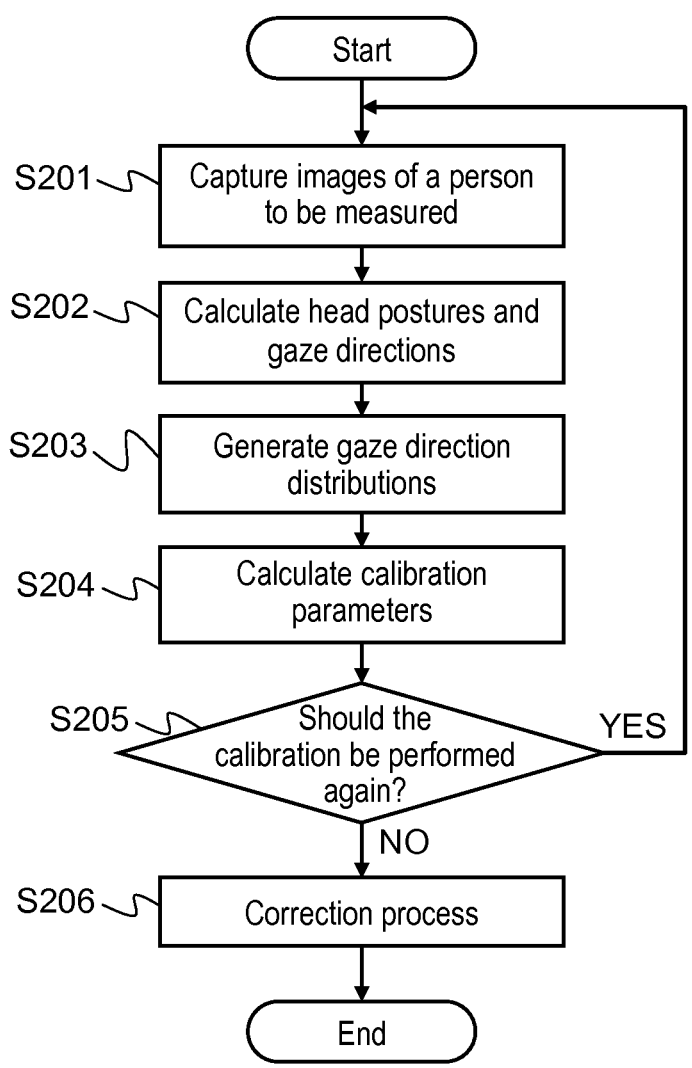
FIG. 2 is a flowchart showing a flow of processing of the gaze detector in the first exemplary embodiment of the present disclosure.

FIG. 2 is a flowchart showing a flow of processing of the gaze detector in the first exemplary embodiment.

First, imaging unit 110 captures images of person A to be measured (step S201).

Next, detector 120 calculates the head postures and the gaze directions of person A to be measured from the captured images (step S202).

The head postures are calculated in such a manner that feature points of a face, for example, tail of eyes, inner corner of eyes, and a corner of mouth are calculated by a template matching method, a statistical patter recognition method, or the like and that three-dimensional positions of the feature points are calculated. As the method for measuring the three-dimensional positions of the feature points, there may be selected a method from a plurality of methods, for example, a stereo method using images themselves and a method using a separately prepared distance measuring sensor. Alternatively, the head postures may be calculated by a common method which is not described here.

The gaze directions may be calculated by using a method in which a gaze direction is calculated based on a positional relationship between a midpoint between right and left pupil positions and a center plane of a face. Alternatively, there may be used known methods such as the corneal reflection method or the pupil center corneal reflection method, in which a gaze direction is calculated based on a positional relationship between a reflection image of infrared light projected to the cornea and the pupil center of each eye.

Next, generation unit 130 generates the gaze direction distribution with respect to each of the head postures from the head postures and the gaze directions calculated by detector 120 (step S203). The method for generating the gaze direction distribution will be described later. A form of the distribution can be a probability distribution such as a normal mixture distribution, a histogram, a cluster center after clustering and a number of data included in the cluster, or raw data themselves in the gaze direction.

Note that there is no particular theoretical limitation to a minimum unit with respect to the head posture by which the gaze direction distributions are switched. However, if the minimum unit is very small, the head postures are frequently switched, whereby sufficient amount of data may not be gathered for each of the gaze direction distributions. To the contrary, if the minimum unit is large, the switching of the head postures cannot be precisely handled. Therefore, it is preferable to empirically determine an optimum value, depending on characteristics of a person to be measured or the like.

In addition, the gaze direction distributions may have non uniform resolution such that the gaze direction distributions are finely switched in a certain range of the head posture and switched coarsely in other ranges.

Calibration unit 140 selects at least one head posture (for example, the head posture facing the imaging unit 110) as the reference posture, calibrates the gaze direction distribution with respect to the reference posture, and calculates the calibration parameters (step S204).

Calibration unit 140 determines whether the calibration should be performed again due to, for example, insufficient accuracy of the calibration parameters (step S205), and if the calibration should be performed again, the process returns to step S201 to repeat the processing up to step S205. If the calibration is not performed again, correction unit 150 performs a correction process in which the gaze direction distributions with respect to the head postures other than the reference posture are corrected by using the calibration parameters calculated by calibration unit 140 (step S206).

[1-2-1. How to Generate the Gaze Direction Distribution]

Figure 3:
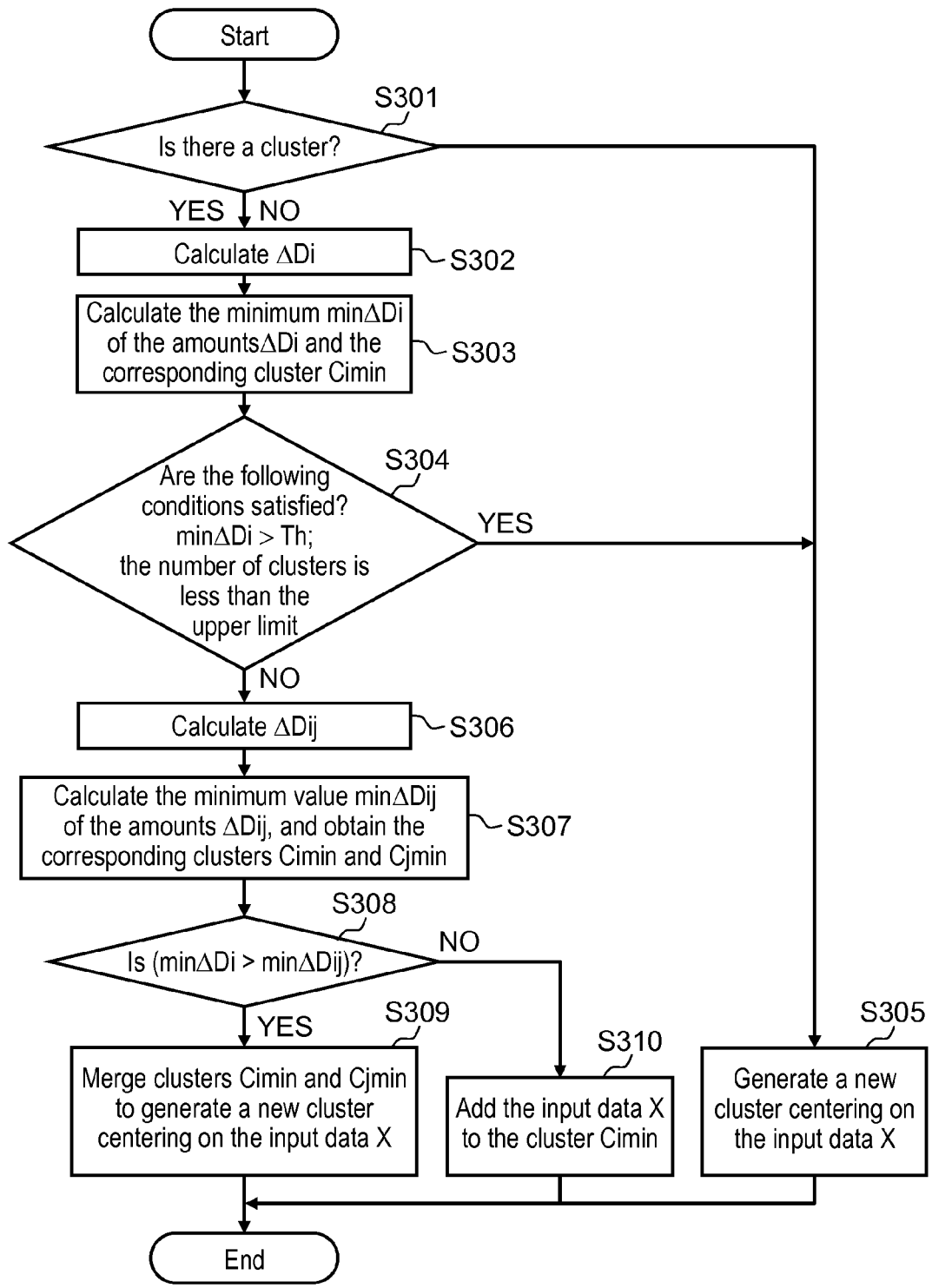
FIG. 3 is a flowchart showing an operation of a generation unit in the first exemplary embodiment of the present disclosure.

In the following, an operation of generation unit 130 will be described with reference to FIG. 3. FIG. 3 is a flowchart showing an operation of generation unit 130 in the first exemplary embodiment.

In the first exemplary embodiment, as a method for generating a gaze direction distribution, there is described an example of a method in which clustering is performed by using an on-line clustering method every time gaze direction data are obtained. Gaze direction data X to be input are expressed by a two-dimensional vector X=(x, y), and a cluster Ci is expressed by a two-dimensional vector Cci= (cxi, cyi) indicating a center of the cluster and a number Ni of data belonging to the cluster, where i is a natural number.

First, when the gaze direction data X are input, generation unit 130 determines whether there is a cluster (step S301), and if it is determined that there is no cluster, generation unit 130 generates a new cluster Cnew centering on the gaze direction data X having been input and finishes the process (step S305).

If generation unit 130 determines in step S301 that there is a cluster, generation unit 130 calculates, by Mathematical Expression 1, an amount ΔDi by which a center of a cluster Ci is moved when the gaze direction data X are added to the cluster Ci (step S302).

$$\Delta D_i = \frac{N_i}{N_i + 1}\{(x - cx_i)^2 + (y - cy_i)^2\} \quad \text{Mathematical Expression 1}$$

Generation unit 130 calculates ΔDi for all the clusters Ci and determines a cluster Cimin which has the minimum value ΔDi, and generation unit 130 records the minimum value of ΔDi as minΔDi (step S303).

Generation unit 130 determines whether minΔDi exceeds a predetermined threshold Th and whether the number of clusters is less than a predetermined upper limit (step S304). If generation unit 130 determines that all the conditions above are satisfied, the process proceeds to step S305, and the generation unit 130 generates a new cluster centering on the gaze direction data X having been input and finishes the process. If generation unit 130 determines in step S304 that all the conditions are not satisfied, the process proceeds to the next step.

Generation unit 130 calculates ΔDij by using Mathematical Expression 2. ΔDij means an amount of movement of the cluster centers of an existing cluster Ci and Cj when Ci and Cj are merged (step S306).

$$\Delta D_{ij} = \frac{N_i N_j}{N_i + N_j}\{(cx_i - cx_j)^2 + (cy_i - cy_j)^2\} \quad \text{Mathematical Expression 2}$$

Generation unit 130 calculates ΔDij for all pairs of the existing clusters and determines a pair of clusters Cimin and Cjmin which has the minimum value ΔDij, and in addition, generation unit 130 records the minimum value of ΔDij as min Δ Dij (step S307).

Finally, generation unit 130 compares the magnitudes of minΔDi obtained in step S303 and minΔDij obtained in step S307 (step S308), if the magnitude of minΔDij is smaller, generation unit 130 merges the clusters Cimin and Cjmin to generate a new cluster centering on the data X having been input (step S309). A cluster Ci' newly made by merging the clusters Ci and Cj has a cluster center represented by the values expressed by Mathematical Expression 3, and the number of data belonging to the cluster is Nimin+Njmin.

$$cx_{i'} = \frac{N_{imin}cx_{imin} + N_{jmin}cx_{jmin}}{N_{imin} + N_{jmin}}$$

$$cy'_i = \frac{N_{imin}cy_{imin} + N_{jmin}cy_{jmin}}{N_{imin} + N_{jmin}}$$

Mathematical Expression 3

On the other hand, if generation unit 130 determines in step 308 that the magnitude of minΔDij is equal to or smaller than the magnitude of minΔDij, generation unit 130 adds to the cluster Cimin the gaze direction data X having been input (step S310). The center of the cluster Cimin is represented by the values expressed by Mathematical Expression 4, and the number of data belonging to the cluster becomes Nimin+1.

$$cx_{imin} = \frac{N_{imin}cx_{imin} + x}{N_{imin} + 1}$$

$$cy_{imin} = \frac{N_{imin}cy_{imin} + y}{N_{imin} + 1}$$

Mathematical Expression 4

A practical meaning of the two-dimensional vector can be the followings: (1) horizontal and vertical angles of the gaze direction; and (2) coordinates of a gazing point on a gazing surface which is virtually disposed at a position a predetermined distance away from person A to be measured. The above-described process can be applied to any one of the two above.

Although an upper limit is set on the number of clusters in the above description, the upper limit does not need to be set. In that case, it can be thought that the conditions about the number of clusters are always satisfied in the determination in step S304.

[1-2-2. Calibration Process]

In the following, an operation of calibration unit 140 will be described with reference to FIG. 4 to FIG. 6.

Figure 4:
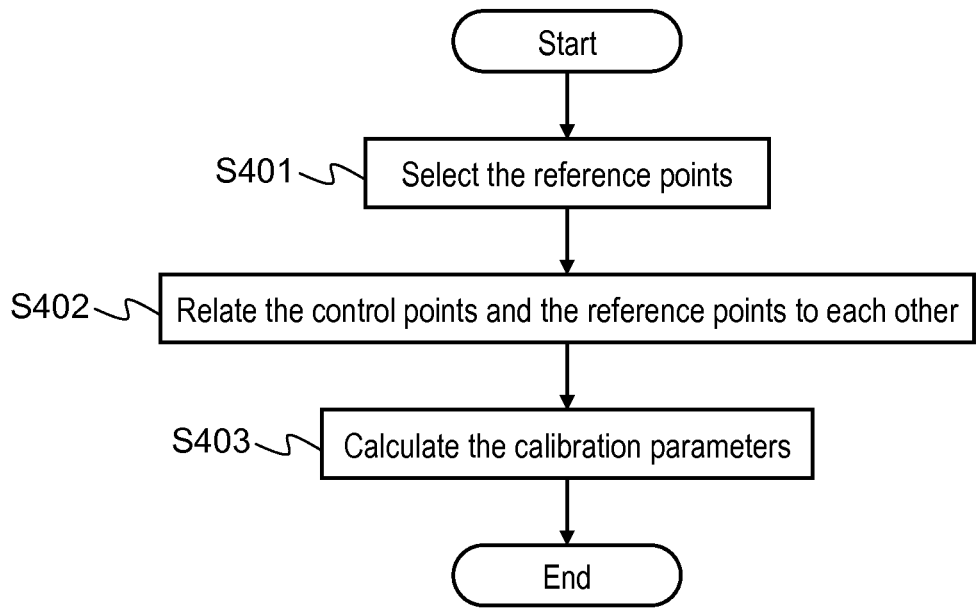
FIG. 4 is a flowchart showing an operation of a calibration unit in the first exemplary embodiment of the present disclosure.

FIG. 4 is a flowchart showing the operation of calibration unit 140 in the first exemplary embodiment. FIG. 5 is a schematic diagram showing a circumscribing rectangle used to determine a positional relationship between the reference points. FIG. 6 is a schematic diagram showing examples of the control points and the reference points.

First, calibration unit 140 selects a predetermined head posture (for example, a head posture facing the imaging unit 110) as the reference posture, and selects the reference points, of the same number as the predetermined control points, from the gaze direction distribution with respect to the reference posture (step S401). Here, the control point is at least one point constituted by a known direction or a position of a calibration target. The method to select the reference points depends on what kind of form the gaze direction distribution is in. For example, in the case that the gaze direction distribution is expressed by a normal mixture distribution, if the gaze direction distribution is previously expressed by a normal distributions of the same number as the reference points, the peak position of each normal distribution naturally becomes each of the reference points.

Alternatively, in the case that the gaze direction distribution is expressed by a histogram, there may be a method in which, for example, the gaze directions with high frequencies are selected as the reference points. In the case that the gaze direction distribution is expressed by raw data or clusters generated by clustering the raw data, there may be a method in which clustering is repeated until the number of the clusters becomes the number of the reference points and in which each cluster center is selected as each of the reference points.

Next, calibration unit 140 evaluates the positional relationship between the reference points to determine to which control point each reference point should be made to correspond (step S402). As the method to evaluate the positional relationship, the following method may be used, for example. One of the reference points which satisfies a specific condition such as having the highest frequency is made to correspond to a certain control point without exception, and the other reference points are made to correspond to appropriate control points by checking the positional relationship to the first reference point.

Figure 5:
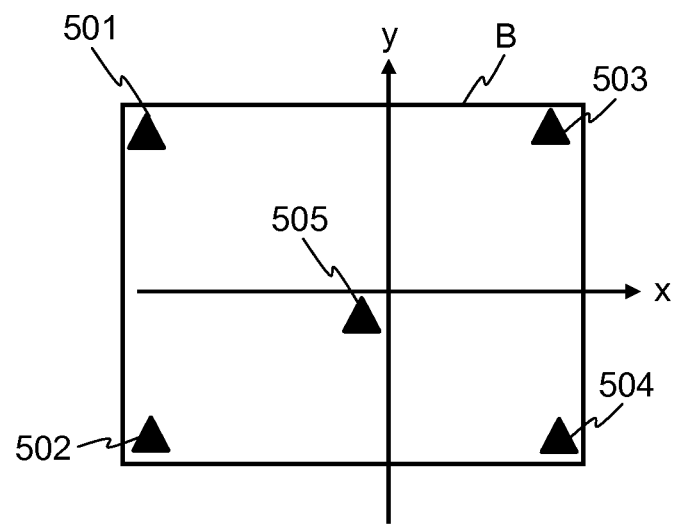
FIG. 5 is a schematic diagram showing a circumscribing rectangle used when a positional relationship between reference points is determined.
Figure 6:
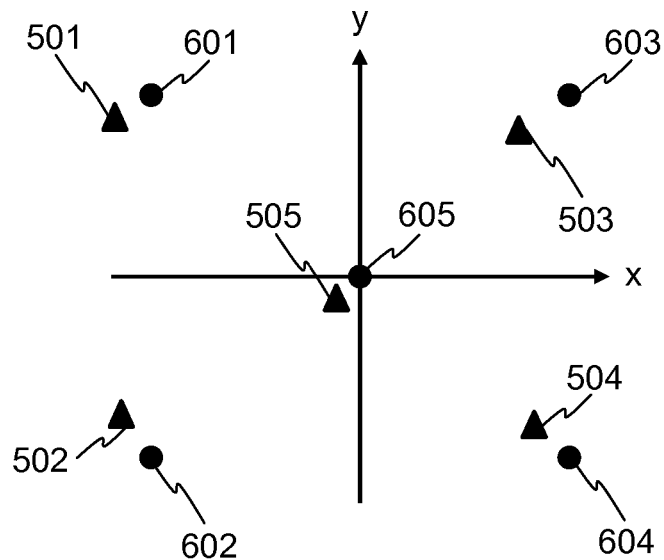
FIG. 6 is a schematic diagram showing examples of control points and reference points.

Alternatively, as shown in FIG. 5, another method may be used, for example, in which a circumscribing rectangle is defined to surround the reference points and in which the relative positions within the circumscribing rectangle are evaluated. In FIG. 5, circumscribing rectangle B is defined to surround five reference points 501 to 505. In this case, the positional relationship between reference points 501 to 505 are evaluated, and reference points 501 to 504 are made to be related to reference point 505.

When the positional relationship between the reference points is determined, calibration unit 140 calculates the calibration parameters which work as transformation parameters for making the reference points correspond to the control e points (step S403). Calibration unit 140 relates control points 601 to 605 to reference points 501 to 505 as shown in FIG. 6, and calculates the calibration parameters with which each of reference points 501 to 505 is made closer to each of control points 601 to 605.

In the following, an example of transformation will be described by using Mathematical Expression 5; however, other transformation equations may be used.

$$\begin{cases} x' = ax + by + c \\ y' = dx + ey + f \end{cases}$$

Mathematical Expression 5

In Mathematical Expression 5, the coordinates (x, y) represent the gaze direction before transformation, and the coordinates (x', y') represent the gaze direction after transformation. The values a to f are the calibration parameters. As the method to determine the parameters, the least square method can be used, for example. In particular, for the k number of control points (X1, Y1), (X2, Y2), . . . (Xk, Yk) and reference points (x1, y1), (x2, y2), . . . (xk, yk), the parameters with which the value of Mathematical Expression 6 is minimized are calculated.

Mathematical Expression 6
$$S = \sum_{i=1}^{k} \{(X_i - (ax_i + by_i + c))^2 + (Y_i(dx_i + ey_i + f))^2\}$$

In this case, the calibration parameters can be obtained by solving the simultaneous equations generated by partially differentiating the right side of Mathematical Expression 6 with respect to each of the parameters and by setting the partially differentiated equations equal to zero.

[1-2-3. Correction Process]

Figure 7:
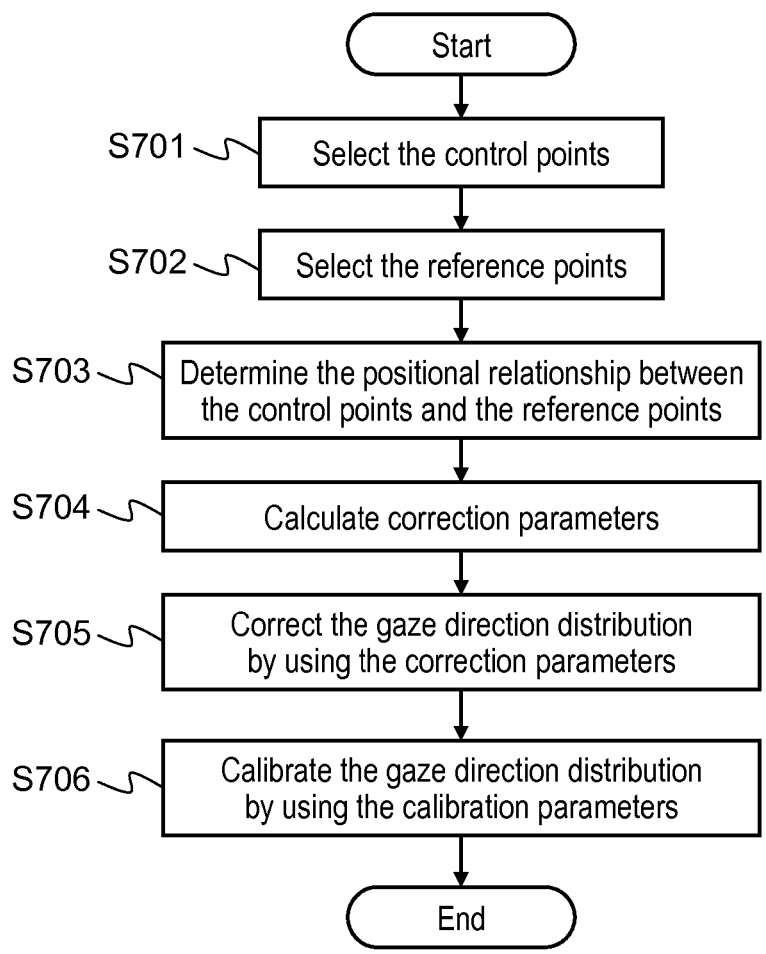
FIG. 7 is a flowchart showing an example of an operation of a correction unit in the first exemplary embodiment of the present disclosure.
Figure 8:
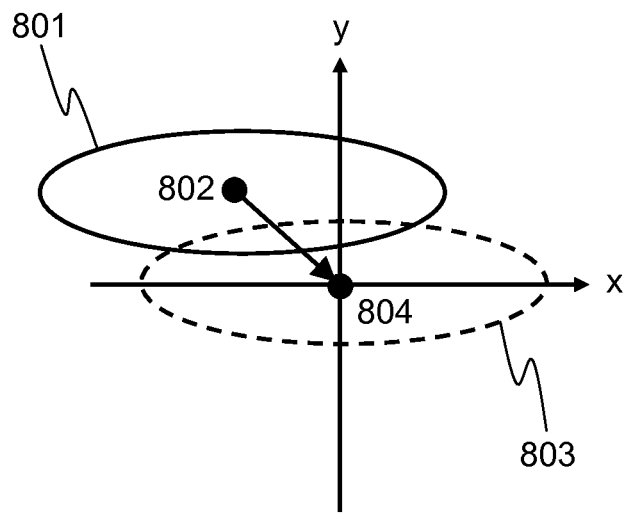
FIG. 8 is a schematic diagram showing an example of a correction process.

In the following, an operation of the correction unit will be described with reference to FIG. 7 and FIG. 8. FIG. 7 is a flowchart showing an example of an operation of the correction unit in the first exemplary embodiment. FIG. 8 is a schematic diagram showing an example of the correction process. Correction unit 150 performs a transformation process to cancel the effect of the calibration parameters, which are different for each of the head postures.

First, correction unit 150 select at least one control point from the gaze direction distribution with respect to the reference posture selected by calibration unit 140 (step S701).

Next, correction unit 150 selects the reference points, of the same number as the control points, from the gaze direction distribution to be corrected (step S702). Correction unit 150 determines the positional relationship between the control points and the reference points in the same manner as the process for calculating the calibration parameters (step S703), and calculates correction parameters for making the control points to correspond to the reference points (step S704).

Here, the same method as in each of step S402 and S403 can be used in each of steps S703 and S704. For example, in the case that a median point of the gaze direction distribution is selected as the control point, there are calculated the correction parameters to be used to perform a transformation so that median point 802 of gaze direction distribution 801 to be corrected (for the head posture other than the reference posture) is moved onto median point 804 of gaze direction distribution 803 for the reference posture as shown in FIG. 8.

Correction unit 150 corrects, by using the correction parameters, the gaze direction distribution to be corrected so that the gaze direction distribution to be corrected is made closer to the gaze direction distribution with respect to the reference posture (step S705), and correction unit 150 then calibrates the reference points by using the calibration parameters calculated by calibration unit 140 (step S706).

As described above, correction unit 150 calculates the calculated correction parameters to be used to perform a transformation in which the gaze direction distributions with respect to the head postures other than the reference posture are made closer to the gaze direction distribution with respect to the reference posture. Then, correction unit 150 corrects the gaze direction distributions with respect to the head postures other than the reference posture by using the calculated correction parameters, and then calibrates the gaze direction distributions with respect to the head postures other than the reference posture by using the calibration parameters.

[1-2-4. Other Examples of the Correction Process]

Figure 9:
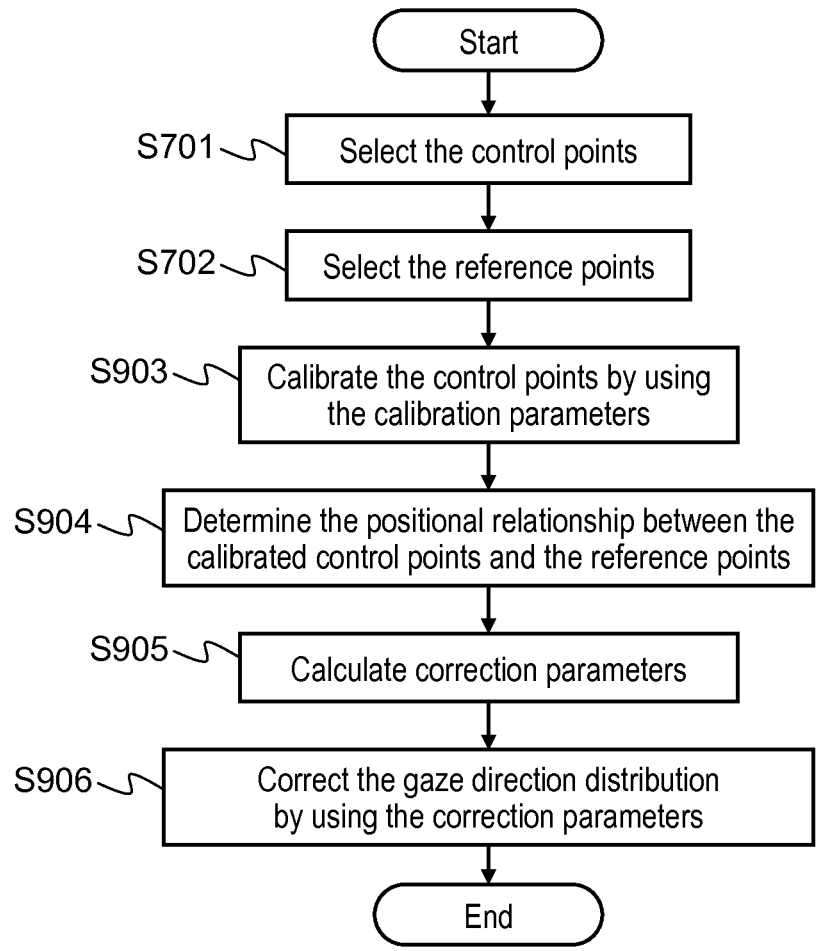
FIG. 9 is a flowchart showing an example of another operation of the correction unit in the first exemplary embodiment of the present disclosure.

In the following, other examples of the correction process will be described with reference to the drawings. FIG. 9 is a flowchart showing an example of another operation of the correction unit in the first exemplary embodiment. Note that the step in FIG. 9 for the same operation as that in FIG. 7 is assigned the same reference numeral, and will not be described again.

The flowchart of FIG. 9 is different from the flowchart of FIG. 7 in that the control points are calibrated after step S702 by using the calibration parameters calculated by calibration unit 140 (step S903) and in that the positional relationship between the calibrated control points and the reference points is obtained (step S904). After that, the correction parameters are calculated to make the calibrated control points and the reference points correspond to each other (step S905).

Correction unit 150 corrects the gaze direction distribution to be corrected by using the calculated correction parameters so that the gaze direction distribution to be corrected is made closer to the calibrated gaze direction distribution with respect to the reference posture (step S906).

Here, correction unit 150 performs the calibration process on the calibrated control points. Thus, the result of the correction process is incorporated into the correction parameters themselves.

[3. Conclusion]

In the gaze detector of the present exemplary embodiment, imaging unit 110 captures images of a person to be measured, detector 120 detects the head postures and the gaze directions of the person to be measured from the images captured by imaging unit 110, generation unit 130 generates the gaze direction distribution for each of the head postures from the head postures and the gaze directions detected by the detector, calibration unit 140 selects the reference posture from the head postures and calibrates the gaze direction distribution with respect to the reference posture to calculate the calibration parameters, and correction unit 150 corrects the gaze direction distributions with respect to the head postures other than the reference posture by using the calibration parameters calculated by the calibration unit.

This arrangement can automatically correct the effect, due to the change of the head postures, given to the result of the calibration.

In addition, the correction unit calculates the correction parameters to be used to perform the transformation in which the gaze direction distributions with respect to the head postures other than the reference posture are made closer to the gaze direction distribution with respect to the reference posture. Then, the correction unit corrects the gaze direction distributions with respect to the head postures other than the reference posture by using the correction parameters, and then calibrates the gaze direction distributions with respect to the head postures other than the reference posture by using the calibration parameters.

Note that it is also possible that the correction unit calculates the correction parameters to be used to perform the transformation in which the gaze direction distributions with respect to the head postures other than the reference posture are made closer to the gaze direction distribution with respect to the reference posture and that the correction unit corrects the calibration parameters by using the correction parameter and then calibrates the gaze direction distributions with respect to the head postures other than the reference posture by using the corrected calibration parameter.

With this arrangement, the result of the calibration process is incorporated into the correction parameters themselves. In this case, the correction unit may perform a transformation in which the median point of the gaze direction distribution with respect to the head posture to be corrected is moved onto the median point of the gaze direction distribution with respect to the reference posture.

Alternatively, it is also possible that the correction unit calibrates the gaze direction distribution with respect to the reference posture by using the calibration parameters and calculates the correction parameters to be used to perform a transformation in which the gaze direction distributions with respect to the head postures other than the reference posture are made closer to the gaze direction distribution with respect to the reference posture. With this arrangement, the result of the calibration process is incorporated into the correction parameters themselves.

The calibration unit makes the control points representing the known gaze direction and the reference points selected from the gaze direction distribution with respect to the reference posture correspond to each other by a predetermined relational expression. The calibration unit may determine the head posture having the highest frequency as the reference posture.

Note that a plurality of reference postures may be determined. In that case, the calibration unit calculates the calibration parameters for each of the plurality of reference postures, and the correction unit uses one of the plurality of reference postures (for example, the reference posture closest to the detected head posture) for processing.

Second Exemplary Embodiment

In the following, a second exemplary embodiment will be described with reference to FIG. 10. Note that the configuration of a gaze detector of the second exemplary embodiment is similar to the configuration of the gaze detector of the first exemplary embodiment, and therefore will not be described again.

[2-1. Operation]

Figure 10:
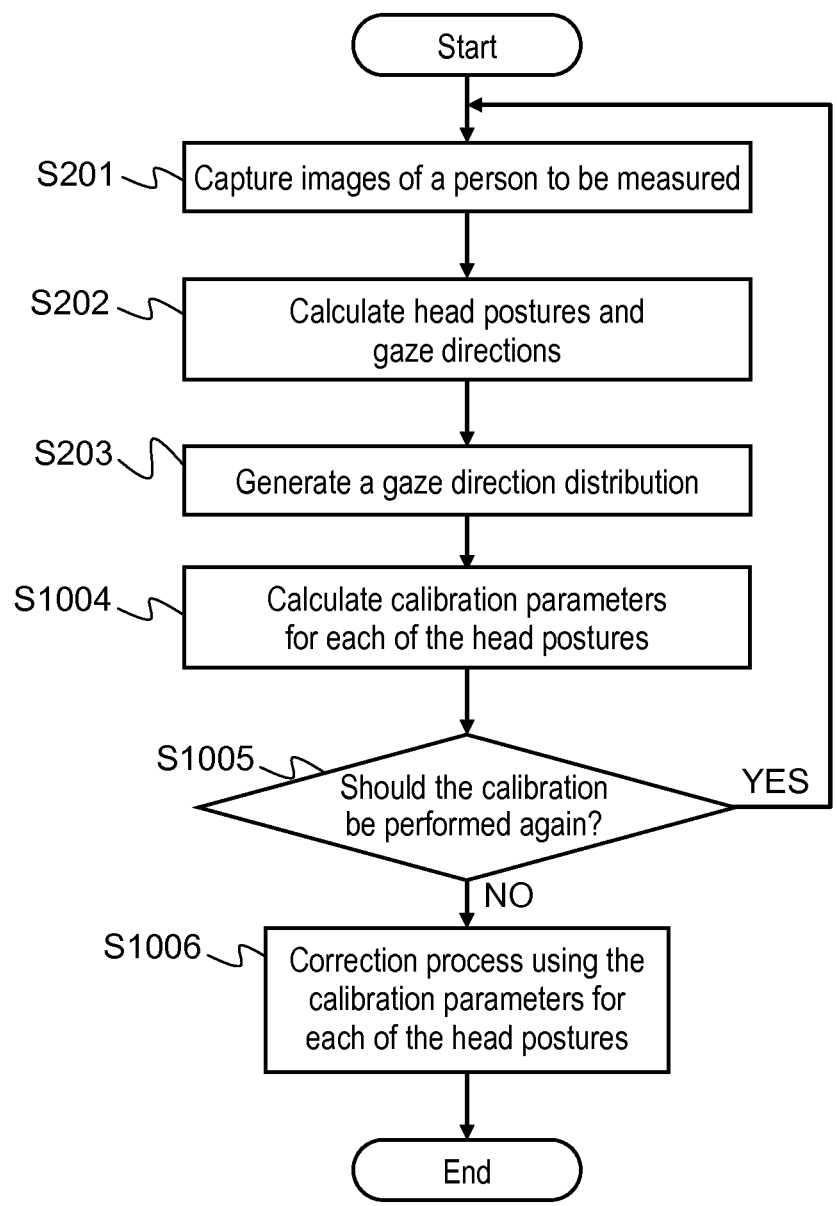
FIG. 10 is a flowchart showing a flow of processing of a gaze detector in a second exemplary embodiment.

FIG. 10 is a flowchart showing a process flow of the gaze detector in the second exemplary embodiment. Note that the step in FIG. 10 for the same operation as that in FIG. 3 is assigned the same reference numeral, and will not be described again.

The flowchart of FIG. 10 is different from the flowchart of FIG. 3 only in step S1004 and after, and calibration unit 140 calculates the calibration parameters to be used to calibrate the gaze direction distribution, with respect to each of the gaze direction distributions with respect each of the head postures (step S1004).

Calibration unit 140 determines whether to perform again the calibration due to, for example, insufficient accuracy of the calibration parameters (step S1005), and if the calibration is to be performed again, the process returns to step S201 to repeat the processing up to this step.

In step S1005, calibration unit 140 may determine the accuracy of only the calibration parameters of at least one specific head posture. With this arrangement, it is possible to proceed the process, ignoring the effect of a head posture which has fewer data in the gaze direction distribution and which tends to lower the accuracy of the calibration parameters.

If the calibration will not be performed again, correction unit 150 corrects the gaze direction distribution by using the calibration parameters with respect to the head postures detected by detector 120 (step S1006).

Note that, in step S1006, there can be a case that the calibration parameters for some detected head postures have not been calculated depending on the process in step S1005.

In that case, correction may not be performed, or correction may be performed by using provisional calibration parameters (for example, Mathematical Expression 5 with a=1, b=0, c=0, d=0, e=1, and f=0 does not change the original gaze direction distribution).

In the gaze detector of the present exemplary embodiment, imaging unit 110 captures images of a person to be measured; detector 120 detects the head postures and the gaze directions of the person to be measured from the images captured by imaging unit 110; generation unit 130 generates the gaze direction distribution for each of the head postures from the head postures and the gaze directions detected by the detector; calibration unit 140 calculates the calibration parameters to be used to calibrate the gaze direction distribution, for each of the gaze direction distributions with respect to each of the head postures; and correction unit 150 corrects the gaze direction distribution by using the calibration parameters which are of the calibration parameters calculated by the calibration unit for the respective head postures and are for the head posture, of the person to be measured, detected by the detector.

This arrangement can automatically correct the effect, due to the change of the head postures, given to the result of the calibration. In the first exemplary embodiment, the calibration parameters are calculated only for the reference posture; however, in the second exemplary embodiment, the calibration parameters are calculated for each of the head postures and are directly used in the correction unit, and the second exemplary embodiment is different from the first exemplary embodiment in this point.

Other Exemplary Embodiments

In the above, the exemplary embodiments are described as examples of the technology disclosed in the present disclosure. However, the technology in the present disclosure is not limited to the above exemplary embodiments and can be applied to an exemplary embodiment in which modifications, replacements, additions, or deletions have been appropriately made. Further, the components described in the above exemplary embodiments can be combined with each other to create a new exemplary embodiment.

Then, other exemplary embodiments will be exemplified below.

For example, when the gaze direction distribution is generated, weighting may be performed depending on time change of the gaze direction. With this arrangement, the state in which the gaze is moving and in which the detection of the gaze direction tends to be unstable can be less weighted, for example, and the gaze direction distribution can be obtained more accurately. Alternatively, only the gaze directions whose time change is smaller than a predetermined magnitude can be used to generate the gaze direction distribution. This arrangement can provide the same effect.

In the above, an example is disclosed in which when the gaze direction distribution is generated, weighting is performed depending on the time change of the gaze direction; however, alternatively, it is also possible to select, in consideration of the weights, the control points and the reference points to be used to calculate the calibration parameters or the correction parameters. In the same manner as the above-described example, this arrangement can provide more accurate positions of the control points or the reference points without using unstable states.

Further, in the gaze detector described in the above exemplary embodiments, each block may be integrated in one chip as a semiconductor device such as an LSI, or all of or a part of the blocks may be integrated in one chip.

The word LSI is used here; however, the semiconductor device may also be called as an IC, a system LSI, a super LSI, or an ultra LSI, depending on the degree of integration.

However, the circuit integration method is not limited to the LSI, and the integration may be realized by a dedicated circuit or a general purpose processor. It is also possible to use an FPGA (Field Programmable Gate Array), which can be programmed after LSI fabrication or to use a reconfigurable processor, in which the connections and settings of circuit cells in the LSI are reconfigurable.

Further, if a technology of circuit integration is developed due to progress of the semiconductor technology or another technology deriving from the semiconductor technology and the technology can replace the LSI, the function blocks may be integrated using such a technology. The bio-technology can be applied in terms of possibility.

The process in the above-described exemplary embodiments may be realized by hardware or alternatively may be realized by software. Instead, the process may be realized by processing by the combination of software and hardware.

The exemplary embodiments are described above as examples of the technology in the present disclosure. For that purpose, the accompanying drawings and the detailed description are provided.

Thus, the components described in the accompanying drawing and the detailed description may include not only the components essential to solve the problem but also the components which are just for exemplify the above technology and not essential to solve the problem. Therefore, those inessential components should not be immediately deemed to be essential because those inessential components are described in the accompanying drawings and the detailed description.

Further, since the above exemplary embodiments are used as examples to describe the technology in the present disclosure, various modifications, replacements, additions, and deletions are possible within the scope of the claims or the equivalents thereof.

The present disclosure is useful for a gaze detector in which a gaze direction of a person to be measured is detected based on an image.

What is claimed is:

1. A gaze detector comprising:
   an imaging unit configured to capture images of a person to be measured;
   a detector configured to detect head postures and gaze directions of the person to be measured from the images captured by the imaging unit;
   a generation unit configured to generate a gaze direction distribution with respect to each of the head postures from the head postures and the gaze directions detected by the detector;
   a calibration unit configured to select at least one reference posture from the head postures and configured to calculate calibration parameters by using the gaze direction distribution with respect to the at least one reference posture; and
   a correction unit configured to correct the gaze direction distributions generated with respect to the head postures other than the reference posture, by using the calibration parameters calculated by the calibration unit.

2. The gaze detector of claim 1, wherein
   the correction unit calculates correction parameters to be used to perform a transformation in which the gaze direction distributions with respect to the head postures other than the reference posture are made closer to the gaze direction distribution with respect to the reference posture, and
   the correction unit corrects the gaze direction distributions with respect to the head postures other than the reference posture by using the correction parameters, and then corrects the gaze direction distributions by using the calibration parameters.

3. The gaze detector of claim 1, wherein
   the correction unit calculates correction parameters to be used to perform a transformation in which the gaze direction distributions with respect to the head postures other than the reference posture are made closer to the gaze direction distribution with respect to the reference posture, and
   the correction unit corrects the calibration parameters by using the correction parameters, and then corrects the gaze direction distributions with respect to the head postures other than the reference posture by using the corrected calibration parameters.

4. The gaze detector of claim 3, wherein the correction unit performs a transformation in which a median point of the gaze direction distribution with respect to the head posture to be corrected is moved onto a median point of the gaze direction distribution with respect to the reference posture.

5. The gaze detector of claim 1, wherein the calibration unit associates a control point representing a known gaze direction with a reference point selected from the gaze direction distribution with respect to the reference posture by a predetermined relational expression.

6. The gaze detector of claim 1, wherein the calibration unit selects one of the head postures most frequently observed as the reference posture.

7. A gaze detector, comprising:
   an imaging unit configured to capture images of a person to be measured;
   a detector configured to detect head postures and gaze directions of the person to be measured from the images captured by the imaging unit;
   a generation unit configured to generate a gaze direction distribution with respect to each of the head postures from the head postures and the gaze directions detected by the detector;
   a calibration unit configured to calculate calibration parameters to be used to calibrate the gaze direction distribution with respect to each of the head postures; and
   a correction unit configured to correct the gaze direction distribution by using some calibration parameters out of the calibration parameters calculated by the calibration unit, the some calibration parameters being with respect to the head postures, detected by the detector, of the person to be measured.

* * * * *